(12) United States Patent
O'Dwyer et al.

(10) Patent No.: US 6,312,931 B1
(45) Date of Patent: Nov. 6, 2001

(54) PROTECTING MOLECULES IN BIOLOGICALLY DERIVED COMPOSITIONS WHILE TREATING WITH HIGH INTENSITY BROAD-SPECTRUM PULSED LIGHT

(75) Inventors: Mary O'Dwyer, Temecula; William H. Cover, Escondido; Jeffrey M. Boeger, Ramona; Karen A. Rieger, Temecula, all of CA (US)

(73) Assignee: Purepulse Technologies, Inc., San Diego, CA (US)

( * ) Notice: Subject to any disclaimer, the term of this patent is extended or adjusted under 35 U.S.C. 154(b) by 0 days.

(21) Appl. No.: 09/502,910

(22) Filed: Feb. 11, 2000

(51) Int. Cl.⁷ .............................. C12N 13/00; C12N 9/14; C12N 9/16; A01N 1/02; C07C 209/00
(52) U.S. Cl. ..................... 435/173.1; 435/2; 435/262.5; 435/195; 435/196
(58) Field of Search ................... 435/173.1, 2, 262.5, 435/195, 196

(56) References Cited

U.S. PATENT DOCUMENTS

| | | | |
|---|---|---|---|
| 4,871,559 | * | 10/1989 | Dunn et al. ............... 426/248 |
| 4,910,942 | * | 3/1990 | Dunn et al. ............... 53/425 |
| 4,946,648 | * | 8/1990 | Dichtelmuller et al. ...... 422/24 |
| 5,489,442 | * | 2/1996 | Dunn et al. ............... 426/248 |
| 5,506,271 | * | 4/1996 | Meruelo et al. ............ 514/732 |
| 5,768,853 | * | 6/1998 | Bushnell et al. ........... 53/167 |
| 5,866,316 | * | 2/1999 | Kempf et al. .............. 435/2 |
| 5,900,211 | | 5/1999 | Dunn et al. ............... 422/23 |

OTHER PUBLICATIONS

Halliwell, Barry, Albumin—An Important Extracellular Antioxidant?, Biochemical Pharmacology, vol. 37, No. 4, pp. 569–571, (1988).
Cover, William H., *Pure Bright® Sterilization System*, a 29-page brochure distributed by PurePulse Technologies, Inc.

* cited by examiner

*Primary Examiner*—David M. Naff
*Assistant Examiner*—Mike Meller
(74) *Attorney, Agent, or Firm*—Fitch, Even, Tabin & Flannery (57) ABSTRACT

A method of protecting a biomolecule from substantial degradation while reducing the content of a pathogen or chemical toxin contained by a biologically derived composition is described. The method involves first providing a biologically derived composition containing a pathogen or chemical toxin and at least one biologically active molecule. Then, adding albumin to the composition to create a supplemented composition. Next, subjecting the supplemented composition to polychromatic pulsed light to degrade the pathogen or toxin. The polychromatic light includes at least one high-intensity, short duration pulse of incoherent polychromatic light in a broad spectrum. The light intensity is at least about 0.01 J/cm², the pulse duration is 10 ns to 100 ms and the light wavelengths are between about 170 nm and about 2600 nm. The content of the albumin in the supplemented composition is such that the subjecting step reduces the content of the pathogen or chemical toxin by at least a factor of 10 without degrading the biological activity of the biomolecule to an unacceptable level. Finally, the biomolecule is recovered in a biologically active state.

21 Claims, 2 Drawing Sheets

PROTECTING MOLECULES IN BIOLOGICALLY DERIVED COMPOSITIONS WHILE TREATING WITH HIGH INTENSITY BROAD-SPECTRUM PULSED LIGHT

BACKGROUND OF THE INVENTION

The use of biologically derived compositions in scientific research and in the manufacture of pharmaceutical/therapeutic substances is ubiquitous. Various human and animal sera are routinely used as a source of protein agents for treatment of various diseases and disorders; for example, to provide desired biomolecules effective as therapeutic agents and for the recovery of antigens that are useful in preparation of vaccines. Tissue culture methods are now commonly employed in the production of numerous pharmaceutical/therapeutic agents and related compositions, such as recombinant DNA and/or recombinant protein (from genetically engineered cell lines), virus vectors, amino acids, peptones, insulin and monoclonal antibodies; the products of such bioreactors require further processing.

Because these compositions are derived from living organisms, including humans, animals, plants and bacteria, they can be contaminated with one or more viruses, bacteria or other pathogens or with chemical toxins generally as result of some processing step. Persons having severely compromised immune systems, such as those with Acquired Immune Deficiency Syndrome (AIDS), are at particular risk for infection from exposure to contaminating pathogens or to chemical toxins in biologically derived compositions. In addition to posing a risk of infection to an individual or an animal receiving such a biologically derived composition, the effectiveness of the composition itself may be compromised by the presence of viral, bacterial and other pathogenic or chemically toxic contaminants.

Recombinant DNA and proteins, monoclonal antibodies, viral vectors and related compositions are also examples of biologically derived compositions used in both research and manufacturing processes that may be contaminated by viruses, bacteria and/or other pathogens. Therefore, in developing pharmaceutical manufacturing processes, steps are usually included to remove or inactivate viruses and other pathogens or toxins that might be present in such biologically derived compositions. Numerous methods of decontaminating or sterilizing biologically derived compositions are presently available, including physical methods, chemical methods, heat methods, irradiation methods and combinations thereof.

Certain well known methods of removing or inactivating viruses, bacteria and/or other pathogens contaminating biologically derived compositions are described, for example, in U.S. Pat. No. 4,540,573 (Neurath, et al.), U.S. Pat. No. 4,946,648 (Dichtelmüller, et al.), U.S. Pat. No. 5,418,130 (Platz, et al.), U.S. Pat. No. 5,527,704 (Wolf, Jr., et al.), U.S. Pat. No. 5,663,043 (Zepp, et al.) and U.S. Pat. No. 5,866,316 (Kempf, et al.). These patents describe combination treatments of biologically derived compositions to inactivate viral and/or bacterial contaminants therein, but include the use of at least one chemical agent to either directly degrade the contaminating organism or to sensitize it for degradation by another chemical agent or heat or radiation. In contrast, the use of light having particular characteristics has more recently been found to be particularly effective and efficient to treat such compositions. For example, U.S. Pat. Nos. 4,726,949, 4,866,282 and 4952,812, Miripol, et al. describe the irradiation of a thin layer of white blood cells with continuous ultraviolet radiation predominately of a wavelength of 280 nm to 320 nm, for about 0.25 to 15 minutes, in order to cause the white blood cells to substantially lose their capability to set off an immune reaction in an alloimmunized patient.

Broad-spectrum pulsed light (BSPL) provides an approach for deactivation of microorganisms and toxins using high-intensity, short-duration pulses of incoherent, polychromatic light in a broad-spectrum. BSPL can also be used to achieve desired rearrangement of biomolecules that are photosensitive to render them more biologically active. BSPL is different from continuous, non-pulsed UV light in a number of ways. The spectrum of BSPL contains UV light, but also includes a broader light spectrum, in particular between about 170 nm and about 2600 nm. The spectrum of BSPL is similar to that of sunlight at sea level, although it is 90,000 times more intense, and includes UV wavelengths between 200 and 300 nm which are normally filtered by the earth's atmosphere. BSPL is applied in short duration pulses of relatively high power, compared to the longer exposure times and lower power of non-pulsed UV light. See for example U.S. Pat. No. 5,034,235 (Dunn et al.), U.S. Pat. No. 5,489,442 (Dunn et al.), U.S. Pat. No. 5,768,853 (Bushnell et al.) and U.S. Pat. No. 5,786,598 (Clark et al.).

BSPL provides biological effects which are different from non-pulsed UV light. For example, pigmented bacteria, such as *Aspergillus niger*, are known to be more resistant to UV radiation than are bacillus spores. In studies using BSPL, however, *Aspergillus niger* was more sensitive, on dry surfaces, to BSPL than were three different bacillus spores: *Bacillus stearothermophilus, Bacillus subtilis* and *Bacillus pumilus*. Further, conventional UV treatment injures DNA by mechanisms that may be reversed under certain experimental conditions classified as either "dark enzymatic repair" or "light enzymatic repair" (Block, S., *Disinfection, Sterilization and Preservation*, $4^{th}$ ed., Williams and Wilkins, U.S.A. (1991)). This photoreactivation by either dark or light enzymes does not occur when BSPL is used to treat microorganisms such as, *Bacillus subtilis, Bacillus pumilus, Aspergillus niger, Clostridium sporogenes, Candida albicans, Staphylococcus aureus, Escherichia coli, Salmonella choleraesuis* and *Pseudomonas aeruginosa*. The presence of wavelengths in the visible range differentiates BSPL from UV light as does the means for generating the two different lights. UV light is usually generated using mercury lamps, which pose some safety hazards; whereas BSPL is commonly generated by lamps using an inert gas, e.g. xenon.

BSPL has been found to be particularly effective in inactivating viruses which are often of greatest concern when manufacturing and using biologically derived compositions. Viruses are frequently grouped based upon their genome, i.e., DNA or RNA viruses, and/or according to the physical characteristic of being enveloped or non-enveloped. Further, individual viruses are generally categorized into a family of viruses with which they share certain evolutionary characteristics. Thus, for example, viruses in the herpes virus family (Herpesviridae) are enveloped DNA viruses, and viruses in the Adenoviridae family are non-enveloped DNA viruses. Examples of enveloped and non-enveloped RNA virus families are, respectively, the Flaviviridae family (which includes Yellow Fever virus, Hepatitis C virus and Bovine Diarrhea virus) and the Picornaviridae family (which includes Poliovirus, Rhinovirus and Hepatitis A virus). Viruses that are most virulent to humans include, for example, Parvovirus, Simian Vacuolating Virus (SV40), Human Immunodeficiency Virus (HIV), Hepatitis Viruses and Bovine Viral Diarrhea Virus (BVDV). BSPL is effective against all of the above.

BSPL has been used to decontaminate and/or sterilize various target objects, such as food products, packages, water and other fluid, semifluid and solid objects. Such is primarily accomplished by placing the target object into, or passing target object through, a BSPL sterilization chamber, and exposing the object to an appropriate number of flashes of BSPL at an appropriate energy level, as described in detail in the above four patents and U.S. Pat. No. 5,900,211 (Dunn, et al.). Its applications are also discussed in detail in the publication "Pure Bright® Sterilization System", W. H. Cover of PurePulse Technologies of San Diego, Calif. (June 1999). While BSPL has been demonstrated to be useful in deactivating various microorganisms, it may also undesirably degrade certain biomolecules of interest, rendering them less biologically active and thus greatly reducing its value in treating particular biologically derived therapeutic and pharmaceutical compositions.

U.S. patent application Ser. No. 09/329,018, filed Jun. 9, 1999, assigned to the assignee of this application, the disclosure of which is incorporated herein by reference, describes methods of inactivating viruses, bacteria and/or other pathogens contained in biologically derived compositions, which methods are effective against a variety of pathogens, especially viruses, and which may be employed in processing a variety of compositions. However, in some instances, the treatment may compromise the effectiveness of the final product, and in cases where such compromising would occur, methods for guarding against such or at least substantially lessening such adverse effect upon the biomolecules of interest are needed.

SUMMARY OF THE INVENTION

The present invention addresses the above and other needs by providing methods for protecting biomolecules of interest when treating biologically derived compositions containing biomolecules of interest with high-intensity, short-duration pulses of incoherent, polychromatic light in a broad-spectrum (BSPL) for purposes of decontamination or otherwise. It has been found that, by adding albumin thereto before subjecting such a supplemented composition to BSPL, substantial degradation of the biomolecule of interest is avoided. By albumin is meant serum albumin and other similar proteins which are functionally equivalent in protecting other molecules from degradation by BSPL. Also provided are the resultant modified compositions containing biomolecules of interest, which composition have, for example, been rendered free of pathogenic or other toxic contamination.

Certain methods of interest reduce, by at least one log, the content of an active pathogen, such as a virus, bacteria, pyrogen, toxin, fungi and/or Protozoa, or other toxin, present in a biologically derived composition along with a biomolecule of interest or kill living eukaryotic cells engineered to produce a protein of interest or tumor cells that may carry a biomolecule of interest. Such methods may comprise adding albumin to a biologically derived composition containing a pathogen or other toxin and at least one biologically active biomolecule of interest to create a supplemented composition, subjecting the supplemented composition to Broad Spectrum Pulsed Light (BSPL) to degrade such pathogen or other toxin, with the content of albumin in the supplemented composition being such that the content of active pathogen or other toxin is reduced by at least a factor of 10 without reducing the biological activity of the biomolecule to an unacceptable level, and recovering the biomolecule in a biologically active state. Preferably, the biomolecule retains at least about 50% of its bioactivity, and more preferably a much higher percentage.

These methods may be advantageously applied to biologically derived compositions such as fermentation broths from bioreactors containing genetically engineered mammalian cell lines, other cell culture material, gene therapy products (such as virus vectors), human and/or animal blood-derived isolates, biological pharmaceutics, such as heparin, peptones, insulin and transferrin, without destroying the therapeutic, pharmaceutical, antigenic, nutritional or other desirable traits of the biomolecule of interest. In particular, sufficient albumin is added to the composition so that proteins, polysaccharides, nucleic acid lipids, monoclonal antibodies and other biomolecules of interest, present in the biologically derived composition, do not lose properties essential for their intended use; in other words, the biomolecules of interest are not irreversibly altered, for example, so that they would no longer exhibit their desirable bioactivity, as a result of exposure to such broad-spectrum pulsed light. Thus, advantageously, the biologically derived composition requires few, if any, additional processing steps as a result of such broad-spectrum pulsed light treatment, one being the optional separation of albumin as a part of the biomolecule recovery.

In one aspect, biomolecules of interest are protected while BSPL efficiently and reliably inactivates viruses, such as, for example, HIV-1 or -2, hepatitis A, B or C, HTLV-I or II or cytomegalovirus, which may be present in biologically derived products. In a further aspect, provided herein are similarly fast, efficient and reliable methods for the inactivation of chemical toxins that may be present in certain previously treated compositions, the addition of albumin followed by exposure to BSPL.

In another aspect, provided herein are methods of activating a photo-activatable protein present in a biologically derived composition together with a biomolecule of interest by first adding albumin and then illuminating the supplemented biologically derived composition with at least one high-intensity, short duration pulse of incoherent, polychromatic light in a broad spectrum.

In a further aspect, methods are provided for protecting at least one biomolecule of interest that needs protection from exposure to BSPL while inactivating at least one pathogen or other toxin present in a biologically derived composition, by adding albumin and then exposing the composition to high-intensity (i.e., 0.01 $J/cm^2$ to 50 $J/cm^2$, e.g., 0.05 $J/cm^2$ to 1.0 $J/cm^2$, wherein energy density is measured at the surface of the composition), short duration (i.e., 10 ns to 100 ms, e.g.,0.3 ms), pulses of incoherent, polychromatic light in a broad-spectrum (i.e., 170 nm to 2600 nm; $1.8 \times 10^{15}$ Hz to $1.2 \times 10^{14}$ Hz). Generally, 1 to 5 pulses will be used.

In a broad aspect, the invention provides a method of protecting a biomolecule from substantial degradation while reducing the pathogenic or otherwise toxic content of a biologically derived composition, which method comprises the steps of providing a biologically derived composition containing a pathogen or other toxin and at least one biologically active biomolecule, which may also contain living eukaryotic cells such as leukocytes, adding albumin to said composition to create a supplemented composition, subjecting said supplemented composition to Broad Spectrum Pulsed Light (BSPL) to degrade said pathogen or other toxin, the content of said albumin in said supplemented composition being such that said subjecting step reduces the content of said active pathogen or other toxin by at least a factor of 10 without degrading the biological activity of said biomolecule to an unacceptable level, and recovering said biomolecule in a biologically active state.

In another particular aspect, the invention provides a biologically derived composition containing a biomolecule of interest which composition has an active viral content reduced by a factor of at least 10 from its original content as a result of treatment with BSPL in the presence of albumin while said biomolecule remains biologically active.

In still another particular aspect, the invention provides a method of using broad-spectrum pulsed light (BSPL) to activate a protein present in a biologically derived composition which also contains a biomolecule of interest, said method comprising the steps of providing a biologically derived composition comprising a photo-activatable protein and at least one biomolecule that is biologically active, adding albumin thereto to create a supplemented composition, and illuminating the biologically derived composition with at least one pulse of BSPL such that said protein is activated without substantially degrading the biological activity of said biomolecule.

In yet another particular aspect, the invention provides a method of protecting a biomolecule while reducing the content of virus or chemical toxin present in a biologically derived composition, which method comprises the steps of providing a biologically derived composition comprising a virus or chemical toxin and at least one biologically active biomolecule of interest, adding albumin to said composition to provide a supplemented composition, and illuminating the supplemented composition with at least one high-intensity, short duration pulse of incoherent polychromatic light in a broad spectrum (BSPL), such that the content of active virus or chemical toxin is reduced by at least a factor of 10 while the biomolecule of interest remains biologically active.

DETAILED DESCRIPTION OF THE PREFERRED EMBODIMENTS

The present invention provides methods for protecting the biological integrity of biomolecules of interest while exposure to BSPL is effected to efficiently inactivate pathogens or other toxins present in biologically derived compositions and/or to activate photo-activatable proteins. It has been found that, by adding a protective amount of albumin to such compositions, high-intensity, short duration pulses of incoherent polychromatic light in a broad spectrum can be used to inactivate viruses, bacteria, other pathogens and/or chemical toxins that might be present in a biologically derived composition, to kill certain eukaryotic living cells, and/or to activate photo-activatable proteins generally without destroying desirable biological properties of biomolecules of interest, such as for example, proteins, polysaccharides, antibodies, nucleic acid lipids and/or peptones in the composition. For example, compositions derived from genetically engineered cell lines, compositions derived through tissue culture processes and related products, e.g. living tissue from transgenic animals, would be potential candidates for such treatment.

By albumin, for purposes of this patent application, is meant serum albumin and other functionally similar proteins which are effective in protecting other molecules from degradation by BSPL. Mammalian serum albumin having about 580 amino acid residues and other equivalent serum albumins, such as fish, amphibian and reptilian serum albumins, are preferably employed. Bovine serum albumin (BSA) is a readily available source of serum albumin which is commonly used in in vitro biological studies, and along with human albumin is more preferred. Albumin is generally added to provide a concentration of between about 1 milligram (mg)/ml and about 75 mg/ml in the supplemented composition; however, it is presently felt that albumin concentrations between about 5 mg and about 50 mg are preferred. The appropriate level required to provide adequate protection while achieving the desired inactivation of pathogens with BSPL can quickly and easily be determined by testing samples thereof, examples of such testing being set forth in the specific examples that follow. The added albumin may be separated from the biomolecule of interest, if desired, following treatment with BSPL or separation may be omitted depending upon the ultimate application. Methods for such optional separation of albumin are well known in the art, and examples would include filtration and liquid chromatography.

In particular, a biologically derived composition supplemented with albumin is placed into and/or flowed through a broad-spectrum pulsed light treatment apparatus. Within a treatment zone of such apparatus, the composition is illuminated by at least one, preferably two and most preferably three short duration pulses. Pulse duration will be less than about 100 ms and is really an artifact of the lamp used and not critical; commonly, the duration may be about 0.3 ms. The pulses should be of high-intensity, e.g., 0.01 J/cm$^2$ to 50 J/cm$^2$, preferably 0.05 J/cm$^2$ to 2.0 J/cm$^2$, more preferably 0.25 J/cm$^2$ to 1.5 J/cm$^2$, and most preferably 0.5 J/cm$^2$ to 1.0 J/cm$^2$, measured at the surface of the composition. The BSPL is incoherent polychromatic light in a broad spectrum, e.g., 170 nm to 2600 nm; i.e., $1.8 \times 10^{15}$ Hz to $1.2 \times 10^{14}$ Hz. Overall, it is anticipated that commercial methods may employ 1–5 short pulses. As a result of such illumination, the content of active pathogen or other toxin within the biologically derived composition is reduced by at least one log (i.e., a factor of 10) and preferably is reduced by more than 2 logs (i.e., a factor of 100), or a photo-activatable protein becomes activated, while the supplemented albumin protects the biomolecule(s) of interest.

Various apparatus may be employed to practice these BSPL illumination methods. Apparatus designed to provide high-intensity, short duration pulsed incoherent polychromatic light in a broad-spectrum are described, for example, in the '235 patent, '442 patent, '853 patent, '442 patent, '853 patent, '598 patent and U.S. Pat. No. 5,900,211. Common to the apparatus used to provide broad-spectrum pulsed light treatment are that the treatment chamber is preferably light-tight; flashlamp(s) are positioned within the apparatus such that the light being emitted therefrom is optimally directed at the target; reflective material is preferably employed to further maximize the pulsed light directed towards the target; and transmissive materials (i.e., quartz, sapphire or similar material) are employed where material is required between the flashlamps and target (such as supporting structures for holding or transporting target material within the chamber).

Of particular importance in designing or selecting apparatus for BSPL treatment is the configuration of the treatment zone of the apparatus, that is, the area within the apparatus where the target material is to be illuminated with the pulsed light. Because the pulsed light should illuminate the entire volume of the target material, the treatment zone will generally be designed to maximize the pulsed light that will reach to the target. For example, where more than one flashlamp is employed simultaneously to illuminate the target material, the treatment zone will preferably be designed so that the target is about equidistant from each flashlamp and so that flashlamps are preferably positioned to surround the target. In order to ensure that pulsed light illuminates the entirety of the target material, structures employed to support the target material within the treatment zone are preferably formed of material that is at least about 1%, preferably at least about 10%, more preferably at least about 50% and most preferably at least about 85% transmissive to BSPL.

Figure 1:
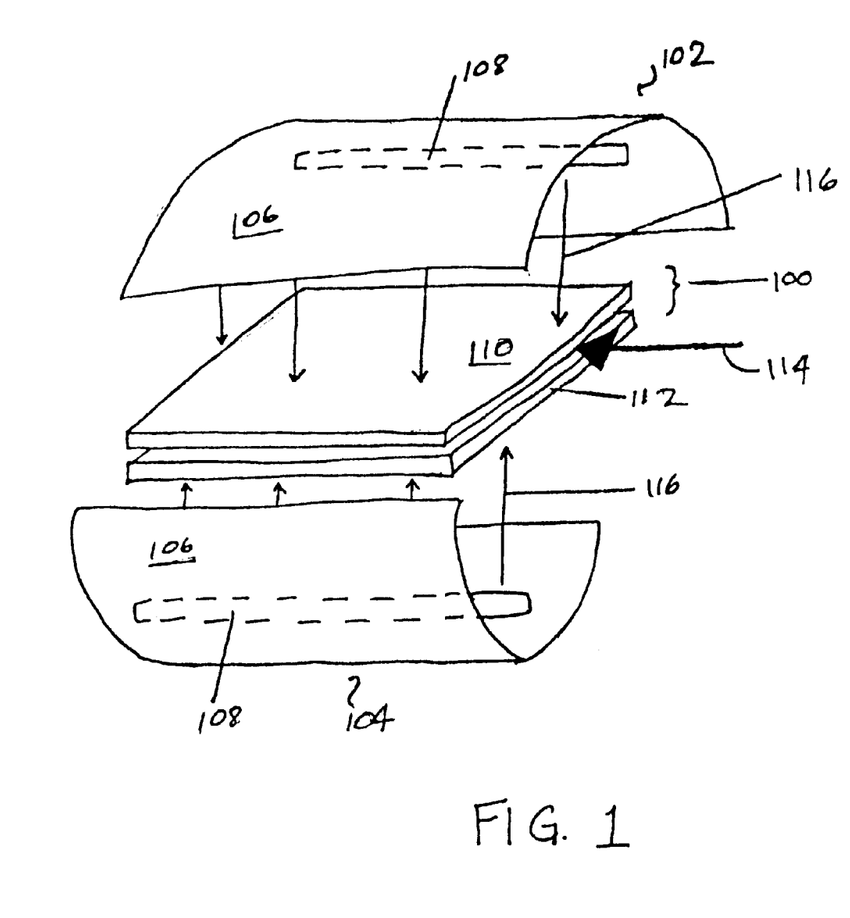
FIG. 1 is a schematic view of the treatment zone of an exemplary pulsed light processing apparatus that may be used to expose biologically derived compositions to BSPL in accordance with the present invention for purposes of decontamination or photo-activation of proteins, which apparatus employs thin, closely spaced plates within which the composition flows as it is treated.

FIG. 1 shows a schematic view of a treatment zone of a preferred exemplary apparatus for use in treating biologically derived compositions with BSPL. In this preferred apparatus, two thin (i.e., less than about 5 mm, for example, about 2 mm) transmissive plates 110, 112 are positioned generally parallel to one another and spaced very closely together (i.e., less than about 5 mm apart, e.g. about 1 mm) to provide a passageway or conduit 100 through which the composition to be treated may pass. On opposite sides of the plates 110, 112 are two flashlamp systems 102, 104, each including a reflector 106 partially surrounding a flashlamp 108. Such flashlamp systems are commercially available, for example, from PurePulse Technologies of San Diego, Calif. as PUREBRIGHT Model No. PBS-1.

The flashlamps 108 are preferably elongated, and a flow of an albumin-supplemented biologically derived composition (illustrated by the arrow 114 in FIG. 1) is preferably caused to occur in a direction parallel to the elongated flashlamps. The plates 110, 112 are preferably fixed to each other along their two opposing edges that are parallel to the flashlamps so that a composition passing therebetween is contained in the passageway created therebetween; a suitably transmissive gel, such as for example, agarose, may be employed to seal the edges. In lieu of parallel plates, a generally rectangular transmissive conduit (e.g., quartz or sapphire) may be employed to transport the composition through the illustrated treatment zone. While only two flashlamp systems 102, 104 are illustrated, additional systems may be employed; for example, the passageway 100 may be surrounded by pulsed light sources. In either case, the light emitted from the flashlamp systems 116 is directed towards the biologically derived composition as it passes through (or resides in) the passageway 100, thereby inactivating viruses and/or other microorganisms or toxins contained therein and/or activating photo-activatable proteins that may be present. Advantageously, by spacing the plates 110, 112 of the passageway 100 close together, the composition being treated is spread into a thin layer, thereby facilitating exposure of the entirety of the composition to the pulsed light, even when the composition is relatively non-transparent and/or undiluted. If it were desired to position flashlamps, for example, only above the passageway 100, then only the upper plate 110 need be transmissive and the lower plate might be opaque.

Figure 2:
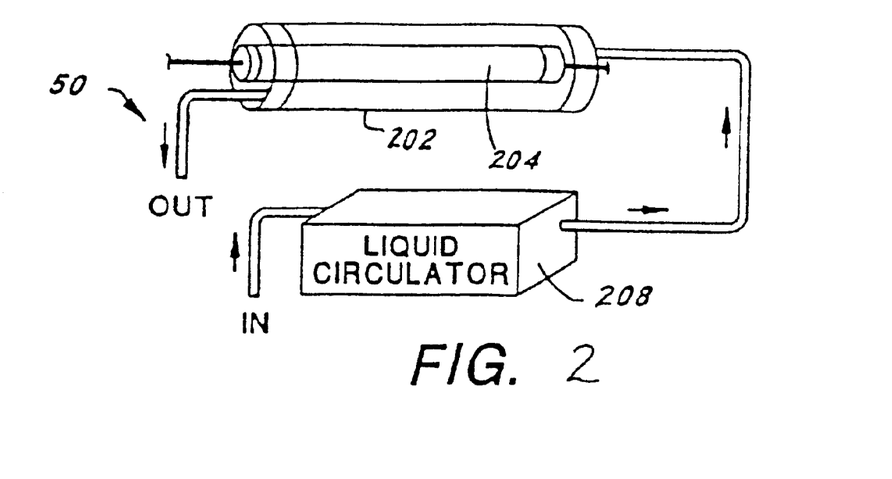
FIG. 2 is a schematic view of another exemplary pulsed light processing apparatus useful herein, which apparatus is useful to treat biologically derived compositions flowing longitudinally through a jacket surrounding an elongated, incoherent pulsed light source that provides high-intensity, short-duration pulses of polychromatic light in the broad-spectrum.

FIG. 2 shows a schematic view of another exemplary apparatus 50 that may be employed to illuminate such compositions containing a biomolecule of interest supplemented with albumin. The apparatus 50 comprises a reflective, cylindrical enclosure defining a treatment chamber 202 through which the composition flows surrounding a pulsed light source 204. The pulsed light source is a high powered xenon flashlamp provided with a suitable power source (not shown) in accordance with conventional practice for flashlamp operation.

A liquid circulation pump 208 controls the flow rate of the composition through the treatment chamber 202 in relation to the pulse repetition rate of the pulsed light source 204 so that, during the time the composition resides within the treatment chamber 202, all of the product that passes therethrough is exposed to a predetermined number of high-intensity, short-duration pulses of incoherent polychromatic light in a broad-spectrum. Very generally, the albumin-supplemented composition being treated will be pumped through the chamber at a flow rate of about 1–4 liters/min.

The product treatment chamber 202 may be arranged so as to be separate from the pulsed light source 204 to prevent the composition therein from contacting the light source 204. Such may be achieved, for example, by employing a quartz jacket (or quartz cylinder) around the light source 204, with the composition being treated passing outside the quartz jacket. Cooling water may be circulated between the light source 204 and the quartz jacket, if desired.

The diameter of the treatment chamber will vary depending upon many factors including but not limited to the specific absorption characteristics of the composition to be treated, the physical and operating characteristics of the light source 204, i.e., flashlamps, and the degree of product mixing between pulses, i.e., flashes, of light. The treatment chamber 202 may include a reflector assembly as its outer wall or as an external reflector, in order to reflect illumination traversing the composition back toward the composition flow path. When an external reflector is used, the reflector assembly may include a quartz (or other transmissive material) cylinder (or tube) inside which the composition is circulated and outside of which the external reflector is positioned.

Some biologically derived fluids, either natural or following dilution, may be relatively transparent to light, including significant portions of the UV spectrum, so that there will be relatively little attenuation through absorption in such compositions, as a result of which the flux density decreases largely only as a function of distance from the light source. Other compositions may exhibit significant absorption, and flux density will additionally decrease as a function of such composition's absorption. However, transmissivity of the composition is not considered to be a potential problem as reflectance should assure adequate illumination throughout. In any event, a desired minimum flux density, e.g., about 0.4 or 0.5 J/cm$^2$ (or even as low as 0.1 or about 0.25 J/cm$^2$ depending on the purpose of the illumination treatment) is preferably maintained throughout the treatment zone. Alternatively or in addition, mixing, e.g. turbulent flow, should occur to insure that all of the fluid being treated is subjected to the desired number of pulses and flux intensity to achieve the desired degree or level of pathogen inactivation or protein photo-activation.

Figure 3:
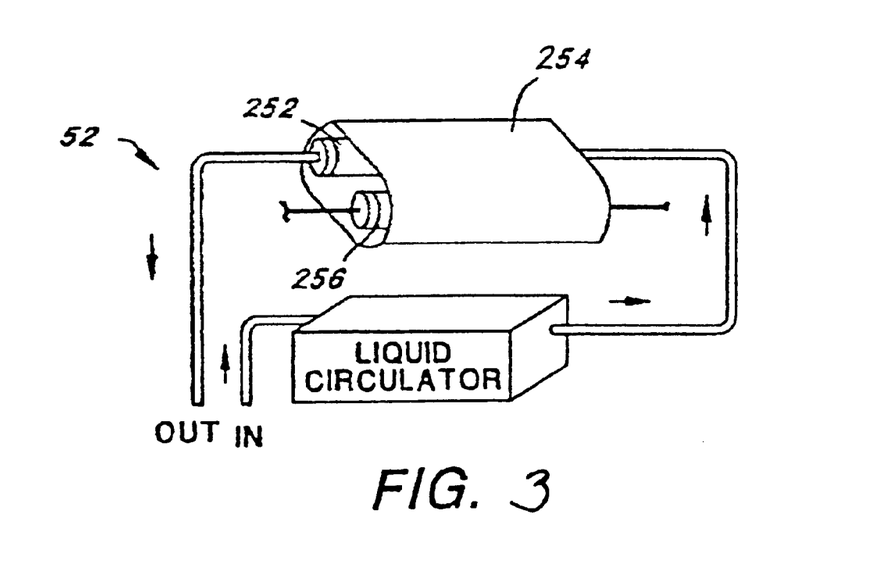
FIG. 3 is a schematic view of still another exemplary pulsed light processing apparatus, wherein a biologically derived composition is caused to flow in a direction parallel to one or more elongated incoherent light sources, within an elliptical reflector, and is treated with high-intensity, short-duration pulses of polychromatic light in a broad-spectrum.

While the flashlamp 204 is located internally of the treatment chamber 202 in the apparatus 50 of FIG. 2, FIG. 3 shows that one or more flashlamps 256 may alternatively (or in addition) be located externally of a treatment chamber 252. A preferred design is shown in which the albumin-supplemented composition being treated is conducted through a treatment chamber 252 employing a transmissive treatment conduit (e.g., a quartz tube) 252. The treatment chamber 252 is positioned along one focus of an elliptical reflector 254, and a flashlamp 256 is positioned along the other focus thereof. The flashlamp 256 may optimally be jacketed in a quartz tube to water cool it. Because the light pulses are focused by the elliptical reflector 254 toward the center of the treatment chamber 252, compensation is provided for the light absorption of the composition being treated, so that the entire volume of the composition flowing therethrough is subjected to uniform light treatment. In a variation (not shown) of the embodiment shown, multiple elliptical reflectors, each having a flashlamp at one focus and the treatment chamber 252 at the other focus, may be utilized if desired.

While various apparatus useful in practicing the methods of the present invention have been described, it will be appreciated by those of skill in this art that various other apparatus, including combinations of the above-described apparatus, may alternatively be employed for these purposes and thus, are equally contemplated herein.

In such treatment apparatus, BSPL is often employed to illuminate and thereby treat a biologically derived composition to reduce the content of active pathogen or chemical toxin, for example virus and/or bacteria, by at least a factor of ten. Preferably, the treatment method comprises illuminating the albumin-supplemented, biologically derived composition with pulsed light having an intensity of at least about 0.01 J/cm$^2$, preferably at least about 0.05 J/cm$^2$, more preferably at least about 0.25 J/cm$^2$, and most preferably at least about 0.5 J/cm$^2$, wherein the energy intensity is measured at the surface of the composition being illuminated.

The light pulses are preferably of very short duration, and pulse duration may be fairly widely varied as it is essentially an artifact of the flashlamp being used. Pulse durations not greater than about 100 milliseconds (ms) are preferred; durations of not greater than about 10 ms, e.g. about 10 ns to about 10 ms, are more preferred, with pulse durations of about 0.3 ms being commonly used. In addition to the pulsed light being of high-intensity and short duration, it should be characterized as incoherent, polychromatic light in a broad spectrum. Preferably, the light includes wavelengths from about 170 nm to about 2600 nm (i.e., frequencies of about $1.8 \times 10^{15}$ Hz to about $1.2 \times 10^{14}$ Hz).

The time between pulses may be very short, e.g., less than about 100 ms, so that a multi-pulse treatment of an albumin-supplemented composition can be completed in less than a minute. If the treatment is of a flowing product being pumped or otherwise circulated (as opposed to a batch treatment), it may be desirable to provide a plurality of flashlamps spaced along the flow path to permit a faster rate of flow. Such short treatment time is in particular sharp contrast to heretofore known methods of reducing the content of active pathogens in biologically derived compositions, which treatments often required hours to complete.

In order to most efficiently and reliably treat biologically derived compositions in accordance with the methods herein, the entire volume of composition should be illuminated as fully as possible by the broad-spectrum pulsed light. Thus, to avoid blocking illumination from reaching the surface of the composition being treated, it should be contained by material that is sufficiently transmissive to BSPL; most preferably, materials at least about 85% transmissive to such broad-spectrum pulsed light are employed. Examples of suitable materials include, for example, polyolefins, such as polyethylene and polypropylene, nylon, quartz and sapphire; the '598 patent discusses various additional polymers suitable for use in contracting pulsed light treatment apparatus.

Different materials may be preferred for forming the containing material depending upon the particular configuration of the pulsed light treatment apparatus in use. For example, where the treatment apparatus employs closely spaced thin plates through which the biologically derived composition passes, such plates are preferably formed of a relatively hard, transmissive material, such as quartz or sapphire. In contrast, where the treatment zone is an intravenous tube, a pliable polymer material will be preferred.

In addition to considering which pulsed light treatment apparatus to use and within which material to contain a biologically derived composition to be treated, certain characteristics of the composition itself should be considered. For example, the transmissivity of the biologically derived composition may be a factor to consider in insuring complete illumination thereof with the broad-spectrum pulsed light. However, even if a biologically derived composition may have reduced transmissivity to broad-spectrum pulsed light, it is believed that there will usually be sufficient reflectivity therein to ensure that adequate illumination is achieved. Moreover, the transmissivity of a biologically derived composition can generally be adjusted by simple dilution. Appropriate dilution techniques as well as techniques for optional reconcentration following treatment with BSPL are well known.

While there may be some lessening of the biological activity of a biomolecule of interest when the supplemented composition is subjected to BSPL, sufficient albumin is added to the composition to be treated so that the concentration of albumin therein is at a protective level so that the biomolecule of interest preferably retains at least about 50% of its bioactivity, more preferably retains at least about 70% thereof, still more preferably at least about 80% thereof and most preferably at least about 90% thereof. Very generally, the addition of greater amounts of albumin, so that there are higher concentrations of albumin in the supplemented composition being treated, will result in greater retention of biological activity; on the other hand, too high concentrations of albumin may prevent the desired level of inactivation of pathogens or other toxins from being achieved or may require higher energy and/or more pulses of BSPL to achieve the desired inactivation levels or the desired level of activation of photo-activatable proteins. These trade-offs will be apparent from the laboratory data that appear hereafter.

If desired, samples of a biologically derived composition to be treated may be supplemented with the desired amount of albumin and then diluted or treated without dilution. Three exemplary methods of introducing the biologically derived composition into a treatment zone for the pulsed light treatment are presented in FIGS. 1 2 and 3, and in addition, batch treatment with optional stirring may be used. Following treatment, optional separation of albumin may be effected.

Specific embodiments of tubular flow methods have been described with respect to FIGS. 2 and 3. In both alternatives, the composition is introduced into the treatment zone of the treatment chamber by pumping through a tube or similar elongated passageway within a cylindrical or an elliptical treatment apparatus. Preferably the tube, at least at the point where the composition is illuminated by pulsed light, has a small enough diameter that the entirety of the composition is illuminated.

In batch treatment, the biologically derived composition is divided into relatively small quantities and placed within one or more appropriately transmissive containers within a treatment zone and illuminated with the pulsed light, with optional stirring depending upon the composition. In the alternative depicted in FIG. 1, plate flow apparatus employs two closely spaced, thin plates in the passageway between which the composition to be treated is caused to flow. This alternative permits treatment of a significant volume of composition at one time by distributing the composition into a thin, wide layer. Other suitable alternatives may also be used.

Following are some specific examples of inactivation of specific pathogens by illumination with BSPL employing various of the methods described herein, together with examples which illustrate the protection of various enzymes by albumin when exposed to representative BSPL treatment and the effectiveness of BSPL to kill $E.\ coli$ in the presence of such protective concentrations of albumin. It has previously been shown that BSPL is effective to inactivate SV-40, HIV-1, CPV and BVD, as well as $E.\ coli$ bacteria in fetal bovine blood serum. Data for two of these experiments is provided for reference purposes and is followed by examples which show that similar inactivation occurs in the presence of different concentrations of albumin. The final examples then illustrate that albumin is indeed effective to protect representative proteins, i.e., enzymes, from substantial loss of biological activity when exposed to pathogen-inactivating doses of BSPL.

EXAMPLE 1

Inactivation of CPV

A-72 cells (ATCC CRL 1542) are inoculated with CPV (ATCCVR-2017). The virus is harvested when 75% to 100% of the cells exhibit cytopathic effects (CPE). Stocks of virus are frozen and stored at −60° C. in a medium containing 10% to 15% FBS.

A-72 cells are used for titration of the samples containing CPV. The medium used for growth and maintenance of A-72 cells is E-MEM supplemented with 5–10% heat-inactivated FBS, 10 mg/ml gentamicin, 100 units/ml penicillin, and 2.5 mg/ml fungizone. Cell cultures are incubated at 36–38° C. in a humidified atmosphere of 5–7% $CO_2$.

A 0.2 mL volume of CPV in E-MEM with 5% heat inactivated FBS is added to sterile polyethylene sample containers. Twelve replicate samples are made. Nine of the samples are treated with BSPL, i.e., incoherent polychromatic light in a spectrum of about 170 nm to about 2600 nm, more than 50% of which has a wavelength below about 600 nm. Of these, three samples are treated with a single light pulse, three samples are treated with two pulses, and three samples are treated with three pulses. Each pulse has an intensity of about 1.0 $J/cm^2$. Three untreated samples serve as controls.

After exposure, a titration is performed by preparing ten-fold dilutions from each viral sample in a 96-well microculture plate seeded with A-72. CPV is allowed to adsorb for 1–2 hours, then removed from the wells and replaced with fresh culture medium. Supernatant samples are transferred from the CPV titration plate to fresh plates for testing by hemagglutination (HA). A titration of RPMI (without phenol red) is performed as a control. All titrations are plated in quadruplicate, monitored for up to 10 days for the presence of CPE and/or cytotoxicity. Results are set forth in Table 1.

TABLE 1

Treatment of CPV with BSPL.

| Replicate # | 0 pulses | 1 pulse | 2 pulses | 3 pulses |
|---|---|---|---|---|
| #1 | | $3.16 \times 10^2$ | No survivors* | $3.16 \times 10^2$ |
| #2 | $1 \times 10^6$ | $3.16 \times 10^2$ | No survivors* | No survivors* |
| #3 | | $3.16 \times 10^2$ | No survivors* | No survivors* |
| AVERAGE | $1 \times 10^6$ | $3.16 \times 10^2$ | No survivors* | $1.26 \times 10^2$ |

*The detection limit of trhis test was $\leq 3.16 \times 10^1$.

Post-exposure titrations are compared to the pre-exposure titration, in order to determine if viral infectivity was reduced by exposure to BSPL. Example 1 shows that 3 to 4 log reduction of CPV occurred using BSPL.

The highest available titre is used in this example. Greater reduction of viruses is expected when higher starting titres are used, more pulses are applied, or the medium is diluted to a lower concentration of protein.

EXAMPLE 2

Inactivation of $E.\ coli$

A sample of 15% FBS was inoculated with $E.\ coli$ (ATCC26) and permitted to grow overnight, at 32° C., to a final concentration of $8.8 \times 10^4$ CFU/ml (4.9 log CFU/ml). 200 μl of the contaminated sample (containing 17,600 CFU, i.e., 4.25 log CFU) was then illuminated with 3 short-duration pulses of broad-spectrum light (1.0 $J/cm^2$/flash) in accordance with the methods described herein so that the entirety of the composition was illuminated. Serial dilutions (10×) of the sample were made (using 0.05M phosphate buffer) and plated onto standard agar plates. The plates were incubated at 32° C. and counted at 24 and 48 hours.

After 48 hours of incubation, no surviving $E.\ coli$ was observed on any plates. Given a sensitivity level of 20 CFU (i.e., 1.3 log CFU), this test demonstrated that treatment of $E.coli$-innoculated FBS, with just 3 pulses of broad-spectrum light resulted in about a 3 log reduction in bacterial content. (4.3 log CFU −1.3 log CFU=3.0 log CFU.)

EXAMPLE 3

Inactivation of $E.\ coli$ in the Presence of BSA

Five compositions are made up containing, respectively, 5, 25, 50, 75 and 100 milligrams of BSA per milliliter of deionized water. Overnight culture of $E.\ Coli$ grown up in TSB (Tryptic Soy Broth) is added to each of the five compositions such that the resulting concentration of $E\ coli$ in each is >6 log CFU/ml. Samples from each of these supplemented compositions are then taken and treated with BSPL using different numbers of flashes and/or different pulse intensities varying from 0.25 $J/cm^2$ per flash to 1.5 $J/cm^2$ per flash. Each time three duplicate samples are treated, and the results are averaged. Three controls are run for each BSA concentration and the results also averaged. Following plating as set forth in Example 2 and incubation at 32° C., counts of CFU were taken after 48 hours. The results are set forth in Table A which follows:

TABLE A

Treatment of E. coli suspended in BSA solutions
LOG SURVIVAL

| J* | Flashes | BSA mg/ml | | | | |
|---|---|---|---|---|---|---|
| | | 5 | 25 | 50 | 75 | 100 |
| Cntl. | N.T.** | 6.7 | 6.1 | 6.2 | 6.2 | 6.3 |
| 0.25 | 1 | 2.9 | — | — | — | — |
| 0.25 | 2 | 1.3 | — | — | — | — |
| 0.5 | 1 | 0.1 | — | — | — | — |
| 0.5 | 2 | N.S.*** | — | — | — | — |
| 1.0 | 1 | N.S.*** | — | — | — | — |
| 1.0 | 2 | N.S.*** | — | — | — | — |
| 1.5 | 3 | — | N.S.*** | N.S.*** | 4.7 | 5.2 |
| 1.5 | 5 | — | N.S.*** | N.S.*** | 3.0 | 4.4 |
| 1.5 | 7 | — | N.S.*** | N.S.*** | 0.6 | 3.6 |

*Joules per cm² per flash
**No Treatment
***No Survivors

The results show that there is 6.6 log kill with a single flash of 0.5 J/cm² intensity in the presence of 5 mg/ml of BSA, greater than 5 log kill with two flashes of 0.25 J/cm², and a log reduction of nearly 4 with only a single flash at that intensity. When greater concentrations of BSA are included, i.e. 25–50 mg/ml, complete kill is achieved by 3 or more flashes of 1.5 J/cm² intensity. At concentrations of about 75 to 100 mg/ml of BSA, additional flashes are required, but log reductions of at least 2.7 are readily achieved.

EXAMPLE 4
Protection of Acid Phosphatase by Albumin

Lypholized acid phosphatase was purchased from Sigma Chemical Co. (St. Louis, Mo.) and reconstituted in filtered deionized water, aliquoted and stored at −20° C. until needed. Approximately 25 U/L (international units) of enzyme was used in each experiment, by appropriately diluting it into either filtered deionized water or 5 mg/ml BSA solutions.

Treatment was carried out by illuminating each sample with BSPL having intensities of 0.5 J/cm², 1.0 J/cm² or 1.5 J/cm² per flash. Samples were treated with up to 5 pulses of light. All experiments were performed in triplicate and the results averaged.

The activity of the enzyme was assayed using the Sigma Diagnostics Alkaline, Acid and Prosphatase kit (Sigma procedure #104). Recovered activity of the treated enzyme samples was compared to the untreated control, and expressed as a percentage of the control activity. The results with and without BSA are set forth in Table B which follows:

TABLE B

Acid Phosphatase and Serum Abumin

| | | Recovery | |
|---|---|---|---|
| J* | Flashes | Without BSA | With BSA (5 mg/ml) |
| Cntl. | 0 | 100% | 100% |
| 0.5 | 1 | 70% | 94% |
| 0.5 | 2 | 69% | 88% |
| 0.5 | 3 | 60% | 86% |
| 0.5 | 4 | 54% | 82% |
| 0.5 | 5 | 45% | 78% |
| 1.0 | 1 | 62% | 92% |
| 1.0 | 2 | 37% | 83% |
| 1.0 | 3 | 23% | 70% |
| 1.0 | 4 | 13% | 65% |
| 1.0 | 5 | 7% | 57% |
| 1.5 | 1 | 51% | 85% |
| 1.5 | 2 | 21% | 74% |
| 1.5 | 3 | 11% | 62% |
| 1.5 | 4 | 6% | 53% |
| 1.5 | 5 | 4% | 45% |

*Joules per cm² per flash

Examination of the results shows that the presence of a concentration of BSA as low as 5 mg/ml provides extensive protection for the biological activity of acid phosphatase when exposed to pathogen-destroying BSPL as can be seen from these results. Whereas this enzyme would suffer a very large loss in its enzymatic activity from subjection to the amounts of BSPL used, very substantial protection is provided by this small concentration of BSA, consistently without regard to the intensity between 0.5 J/cm² to 1.5 J/cm² and for amounts varying from 1 to 5 flashes. It is expected that the inclusion of higher concentrations, e.g. 10 mg/ml, would provide even further protection.

EXAMPLE 5
Protection of Alkaline Phosphatase by Serum Albumin

Lypholized alkaline phosphatase was purchased from Sigma Chemical Co. (St. Louis, Mo.) and reconstituted in reconstitution buffer containing 10 mm Tris, 50 mm NaCl, 1.5 mm CHAPS, pH 7.4. This enzyme solution was aliquoted and stored at −20° C. until needed. Approximately 83.5 U/L of enzyme was used in each experiment, by appropriately diluting it into either filtered deionized water or 5 mg/ml BSA solutions.

Treatment was carried out by illuminating each sample with BSPL having intensities of 1.0 J/cm² or 1.5 J/Cm² per flash. Samples were treated with up to 5 pulses of light. All experiments were performed in triplicate, and the results averaged. The activity of the enzyme was assayed using the Sigma Diagnostics Alkaline, Acid and Prostatic Acid Phosphatase kit (Sigma procedure #104). Recovered activity of the treated enzyme samples was compared to the untreated control, and expressed as a percentage of the control activity. The results with and without BSA are set forth in Table C which follows:

TABLE C

Alkaline Phosphatase and Serum Albumin

| | | Recovery | |
|---|---|---|---|
| J* | Flashes | Without BSA | With BSA (5 mg/ml) |
| Cntl. | 0 | 100% | 100% |
| 1.0 | 3 | 86% | 100% |
| 1.0 | 5 | 74% | 98% |
| 1.5 | 1 | 90% | 99% |
| 1.5 | 3 | 52% | 94% |
| 1.5 | 5 | 12% | 84% |

*Joules per cm² per flash

Examination of the results shows that the presence of a concentration of BSA of only 5 mg/ml provides extensive protection for the biological activity of alkaline phosphatase when exposed to pathogen-destroying BSPL as can be seen from the results. Whereas this enzyme would suffer a significant loss in its enzymatic activity from subjection to BSPL, e.g. 1.5 J/cm$^2$, very substantial protection is provided by this concentration of BSA, essentially making practical an intensity of 1.5 J/cm$^2$ for 5 flashes. It is expected that the inclusion of higher concentrations, e.g. 10 mg/ml would provide even further protection.

EXAMPLE 6

Protection of Lactate Dehydrogenase (LDH) by Serum Albumin

Lactate dehydrogenase (LDH) was purchased from Sigma Chemical Co., St. Louis, Mo.), stored as is at 4° C., and aliquots removed as needed. Approximately 900 U/L of enzyme was used in each experiment, by appropriately diluting it into either filtered deionized water or 5 mg/ml BSA solutions.

Treatment was carried out by illuminating each sample with BSPL having an intensity of 0.5 J/cm2 per flash. Samples were treated with up to 5 pulses of light. All experiments were performed in triplicate, and the results averaged. The activity of the enzyme was assayed using the Sigma Diagnostics lactate Dehydrogenase kit (Sigma procedure #500). Recovered activity of the treated enzyme samples was compared to the untreated control, and expressed as a percentage of the control activity. The results with and without BSA are set forth in Table D which follows:

TABLE D

Lactate Dehydrogenase and Serum Albumin

| | | Recovery | |
|---|---|---|---|
| J* | Flashes | Without BSA | With BSA (5 mg/ml) |
| Cntl. | 0 | 100% | 100% |
| 0.5 | 1 | 27% | 100% |
| 0.5 | 2 | 13% | 100% |
| 0.5 | 3 | 4% | 92% |
| 0.5 | 4 | 0% | 84% |
| 0.5 | 5 | 2% | 74% |

*Joules per cm$^2$ per flash

Examination of the experimental results shows that LDH is an example of an enzyme that is highly susceptible to loss of bioactivity when subjected to BSPL at as low an intensity as even 0.5 J/cm$^2$. However, inclusion of a concentration as low as 5 mg/ml BSA in the composition being illuminated provides complete protection of the enzyme for two flashes, recovery of more than 90% after three flashes, recovery of more than 80% after four flashes and recovery of nearly 75% of the biological activity of the enzyme after five flashes. This example illustrates the excellent protection provided by albumin to enzymes that are particularly sensitive to this particular pathogen-destroying method.

While the invention herein disclosed has been described by means of specific embodiments and applications thereof, numerous modifications and variations can be made thereto, by those of skill in the art, without departing from the scope of the invention as set forth in the following claims. The disclosures of all references and U.S. patents are expressly incorporated herein by reference.

What is claimed is:

1. A method of protecting a biomolecule from substantial degradation while reducing the content of a pathogen or chemical toxin contained by of a biologically derived composition, which method comprises:

providing a biologically derived composition containing a pathogen or chemical toxin and at least one biologically active biomolecule;

adding albumin to said composition to create a supplemented composition;

subjecting said supplemented composition to polychromatic pulsed light to degrade said pathogen or toxin, wherein the polychromatic pulsed light includes at least one high-intensity, short duration pulse of incoherent polychromatic light in a broad spectrum wherein the light intensity is at least about 0.01 J/cm$^2$, the pulse duration is 10 ns to 100 ms and the light wavelengths are between about 170 nm and about 2600 nm, the content of said albumin in said supplemented composition being such that said subjecting reduces the content of said pathogen or chemical toxin by at least a factor of 10 without degrading the biological activity of said biomolecule to an unacceptable level, and recovering said biomolecule in a biologically active state.

2. The method according to claim 1, wherein said albumin is added to provide a concentration of at least about 5 mg/ml in said supplemented composition.

3. The method according to claim 1 further comprising separating said albumin from said biomolecule of interest as a part of said recovery step.

4. The method according to claim 1, wherein said pathogen is selected from the group consisting of viruses, bacteria, Protozoa, fungi, prions, and pyrogens.

5. The method according to claim 4, wherein said virus is selected from the group consisting of human immunodeficiency virus (HIV)-1, HIV-2, hepatitis A, hepatitis B, hepatitis C, HTLV-I, HTLV-II, cytomegalovirus, simian vacuolating virus 40, bovine viral diarrhea virus and canine parvovirus.

6. The method according to claim 1, wherein said biologically derived composition comprises living tissue, fermentation broth from a bioreactor, cell culture material or isolates from transgenic or other animals.

7. The method according to claim 1, wherein said biomolecule of interest is selected from the group consisting of Factor VIII, Factor IX, antithrombin, transferrin, immunoglobulin, monoclonal antibodies, viral vectors, heparin, collagen, insulin, enzymes and antigens useful vaccine manufacture.

8. The method according to claim 1, wherein said subjecting comprises the use of at least two of said high-intensity, short duration pulses of incoherent polychromatic light in a broad spectrum.

9. A method of using polychromatic pulsed light to activate a protein present in a biologically derived composition which also contains a biomolecule of interest, said method comprising:

providing a biologically derived composition comprising a photo-activatable protein and at least one biomolecule that is biologically active;

adding albumin thereto to create a supplemented composition; and illuminating the biologically derived composition with at least one pulse of polychromatic light such that said protein is activated without substantially degrading the biological activity of said biomolecule, wherein the polychromatic light includes at least one high-intensity, short duration pulse of polychromatic light having a light intensity of at least about 0.01 J/cm$^2$, a pulse duration of 10 ns to 100 ms and a light wavelength between about 170 nm to about 2600 nm.

10. A method of protecting a biomolecule, when reducing the content of, a virus, a chemical toxin, living cells, combinations thereof, in a biologically derived composition, which method comprises:

providing a biologically derived composition comprising a virus, a chemical toxin living cells, or combinations thereof and at least one biologically active biomolecule of interest;

adding albumin to said composition to provide a supplemental composition; and illuminating the supplemented composition with at least one high-intensity, short duration pulse of polychromatic pulsed light, such that the content of said virus, chemical toxin, living cells, or combinations thereof is reduced by a factor of 10, while the biomolecule of interest remains biologically active, wherein the polychromatic light includes at least one high-intensity, short duration pulse of polychromatic light having a light intensity of at least about 0.01 J/cm$^2$, a pulse duration of 10 ns to 100 ms and a light wavelength between about 170 nm to about 2600 nm.

11. The method according to claim 10, wherein albumin is added to provide a concentration thereof in said supplemented composition between about 1 mg/ml and about 50 mg/ml.

12. The method according to claim 10, wherein said at least one virus is selected from the group consisting of HIV-1, HIV-2, hepatitis A, hepatitis B, hepatitis C, HTLV-I, HTLV-II, cytomegalovirus, SV40, bovine viral diarrhea virus and canine parvovirus and wherein said biomolecule of interest is an expression product of a genetically engineered mammalian cell line.

13. The method according to claim 12, wherein said illuminating is carried out under conditions such that the inactivation of the virus results in at least a two log reduction in active viral content.

14. The method according to claim 10, wherein said illuminating comprises illuminating the supplemented biologically derived composition with at least two of said high-intensity, short duration pulses of incoherent polychromatic light in a broad spectrum.

15. The method according to claim 10, wherein the biomolecule of interest is selected from the group consisting of insulin, transferrin, heparin, collagen, amino acids, peptones, peptides, monoclonal antibodies and enzymes.

16. The method according to claim 10, wherein the biologically derived composition comprises a product of a genetically engineered mammalian cell line which contains a protein that constitutes said biomolecule of interest.

17. The method according to claim 16, wherein said albumin is added to provide a concentration of between about 1 mg/ml and about 50 mg/ml in the supplemented composition, wherein said biomolecule retains at least about 80% of its biological activity following said illuminating, and wherein said biomolecule is recovered.

18. A method for reducing the pathogen content of a biologically derived composition that includes at least one biomolecule having biological activity, the method comprising:

adding albumin to a biologically derived composition containing a pathogen and a biomolecule having biological activity to provide a albumin supplemented biological composition, the albumin being added to the biologically derived composition in an amount effective for preventing a reduction of the biological activity of said biomolecule in the biologically derived composition; and subjecting said albumin supplemented biological composition to polychromatic pulsed light, the polychromatic pulsed light being effective to reduce the pathogen content of said composition by at least a factor of 10, wherein the polychromatic pulsed light includes at least one high-intensity, short duration pulse of polychromatic light having a light intensity of at least about 0.01 J/cm$^2$, a pulse duration of 10 ns to 100 ms and a light wavelength between about 170 nm to about 2600 nm.

19. The method according to claim 18, wherein albumin is added to the biologically derived composition at a concentration between about 1 mg/ml to about 50 mg/ml.

20. A biologically derived composition produced by the method of claim 5.

21. A biologically derived composition produced by the method of claim 9.

* * * * *